United States Patent [19]

Lele et al.

[11] Patent Number: 4,855,911

[45] Date of Patent: Aug. 8, 1989

[54] ULTRASONIC TISSUE CHARACTERIZATION

[75] Inventors: Padmakar P. Lele, Winchester, Mass.; Gerard E. Sleefe, Cedar Crest, N. Mex.

[73] Assignee: Massachusetts Institute of Technology, Cambridge, Mass.

[21] Appl. No.: 121,240

[22] Filed: Nov. 16, 1987

[51] Int. Cl.[4] .................................................. A61B 10/00
[52] U.S. Cl. .................................. 364/413.25; 73/602; 128/660.06; 128/660.07; 364/413.15
[58] Field of Search ...................... 73/602; 128/660.06, 128/660.07; 364/414, 415, 413.13, 413.14, 413.15, 413.21, 413.25

[56] References Cited

U.S. PATENT DOCUMENTS

| | | | |
|---|---|---|---|
| 4,202,215 | 5/1980 | Meyer | 73/599 |
| 4,322,974 | 4/1982 | Abele et al. | 73/602 |
| 4,407,163 | 10/1983 | Hundt et al. | 73/607 |
| 4,409,838 | 10/1983 | Schomberg | 128/660.06 |
| 4,470,303 | 9/1984 | O'Donnell | 73/602 |
| 4,472,972 | 9/1984 | Riley et al. | 73/620 |
| 4,509,524 | 4/1985 | Miwa | 128/660.06 |
| 4,511,984 | 4/1985 | Sumino et al. | 364/415 |
| 4,512,195 | 4/1985 | Miwa et al. | 73/602 |
| 4,542,744 | 9/1985 | Barnes et al. | 128/660 |
| 4,545,250 | 10/1985 | Miwa | 73/602 |
| 4,581,935 | 4/1986 | Breazale | 73/602 |
| 4,619,267 | 10/1986 | Lannuzel et al. | 128/660.06 |
| 4,655,228 | 4/1987 | Shimura et al. | 128/660 |
| 4,658,827 | 4/1987 | He et al. | 128/660 |

OTHER PUBLICATIONS

Lele et al., Tissue Characterization by Ultrasonic Frequency-Dependent Attenuation and Scattering, *Nat'l. Bureau of Standards Pub.* 453, pp. 167–196, Oct. 1976.

Lele et al., The Frequency Spectra of Energy Backscattered and Attenuated by Normal and Abnormal Tissue, *Recent Advances in Ultrasound in Biomedicine*, vol. 1, 1977.

Fellingham, *Ultrasonic Characterization of Tissue Structure in the In Vivo Human Liver and Spleen*, IEEE Trans., vol. SU-31, No. 4 (Jul. 1984).

Kuc, Ultrasonic Tissue Characterization Using Kurtosis, IEEE, vol. UFFC-33, No. 3 (May 1986).

*Primary Examiner*—A. D. Pellinen
*Assistant Examiner*—Jeffrey A. Gaffin
*Attorney, Agent, or Firm*—Thomas J. Engellenner

[57] ABSTRACT

Methods and devices for characterizing tissues and the like utilize signals obtained from ultrasonic backscatter processes. The method accounts for frequency-dependent attenuation, spatially-varying media statistics, arbitrary beam geometries, and arbitrary pulse shapes. Statistical analysis is employed to estimate the scatterer number density (SND) of tissues. The method for estimating the scatterer number density incorporates measurements of both the statistical moments of the backscattered signals and the point spread function of the acoustic system.

29 Claims, 4 Drawing Sheets

ULTRASONIC TISSUE CHARACTERIZATION

The U.S. Government has rights in this invention pursuant to National Cancer Institute Grant No. NCI-CA31303.

This invention concerns non-invasive methods and devices for characterizing body tissue and, in particular, ultrasonic tissue characterization based on scatterer number density estimation.

Since the early 1970's, it has been recognized that the measurement of ultrasonic attenuation and/or scatter characteristics in tissues would be useful for non-invasive tissue characterization. As a result, the quantitative measurement of these acoustic properties in tissue has become an important area of research. The estimation of either the frequency-dependent attenuation of tissues or some aspect of acoustic scatter generally involves the processing of the backscattered radio frequency (r.f.) signals. Unfortunately, no tissue characterization estimation method has become clinically useful due primarily to the lack of understanding of the interactions of a complex acoustic field with a three-dimensional, random-scattering structure.

Further details concerning the background of this invention can be found in an article by the present inventors, P. P. Lele and G. E. Sleefe, entitled "Ultrasonic Tissue Characterization," in *Ultrasound: Medical Applications, Biological Effect, and Hazard Potential*, M. H. Rapacholi, M. Grandolfo, and A. Rindi, Eds., Plenum Press, NY, NY, 1986, herein incorporated by reference.

There exists a need for better methods and devices for non-invasive characterization of body tissues by ultrasound. In particular, an ultrasonic characterization system which can analyze backscattered acoustic signals and derive therefrom an accurate characterization of internal body organs or tissues would satisfy a long need in the art.

SUMMARY OF THE INVENTION

Non-invasive tissue characterization techniques and devices are disclosed based upon the measurement and analysis of backscattered waveforms following acoustic (e.g., ultrasonic) interrogation of the tissue. The method accounts for frequency-dependent attenuation, spatially-varying media statistics, arbitrary beam geometries, and arbitrary pulse shapes.

In one aspect of the invention, statistical analysis can be employed to estimate the scatterer number density (SND) of tissues. The method estimates the scatterer number density by measuring the statistical moments of the backscattered waveform and the point spread function (psf) of the acoustic system. The SND estimate is obtained by a combination of the backscattered waveform's coefficient of excess, $\gamma$, and the volume associated with the system psf.

The performance of the estimation method was experimentally investigated, and there was an excellent agreement between the predicted and calculated values indicating the appropriateness of the model, as well as the accuracy to which SND can be measured. It appears that SND estimation may be preferred over attenuation estimations for tissue characterization purposes since SND is particularly sensitive to tissue type and can be estimated using relatively small tissue volumes.

The scatterer number density (or number of scatterers per unit volume) is obtained by representing the medium as an absorbing matrix material with random scatterers randomly distributed throughout. The geometry of the acoustic field and the temporal response of the transducers can take any arbitrary form. The method represents the backscattered acoustic signals as time-varying, non-homogeneous, filtered Poisson processes.

To verify the present invention, various experimental studies were performed and involved the analysis of signals backscattered from laboratory constructed phantoms with known values of SND and in-vitro mammalian tissue specimens. Using a variety of different ultrasonic transducers and frequencies, the present invention achieved an excellent correlation between predicted and experimental results. The tissue specimens studied were bovine muscle, bovine liver, and pig liver. The measured value of SND for these specimens were found to agree well with histological findings.

Measurements for SND can be used clinically, for example, to differentiate and identify the tissues of various body organs and characterize their pathological state. SND correlates well with the distance between small tissue structures, a parameter known to be affected by many infectious and neoplastic diseases. For example, the present invention can be useful in the diagnosis of chronic liver hepatitis where changes in the interstitial distance between small tissue structures are pronounced, as well as in other viral infections and neoplasty. It also appears to be useful for determination of any changes in tissues or tissue structure from interventional procedures, such as, for example, hyperthermia, focal coagulatory ablation, cryosurgery, laser surgery, phototherapy, radiation therapy, chemotherapy, etc.

In another aspect of the invention, devices are disclosed for detecting backscattered waveforms, analyzing the waveform to estimate the SND and then characterizing the waveform to determine the type and condition of the tissue. The analyzing means computes the statistical moments of the waveform and combines such measurements with a measurement of the point spread function obtained by a-priori measurement or autocorrelation. Tissue characterizations can be effected, for example, by comparing the SND estimate with predetermined parameters (e.g., stored histological data) such as by processing the SND through digital filters of known tissue characteristics until a match is found or by employing decision function logic programmed to match the SND measurement with the most likely tissue characterization.

The invention will next be described in connection with certain illustrated embodiments; however, it should be clear that various additions, subtractions and modifications can be made without departing from the spirit or scope of the invention. For example, although the terms "ultrasound" and "ultrasonic" are used throughout this specification, "sonic" waves (i.e., acoustic waveforms within the audible range) can also be employed. The invention can be practiced with acoustic waveforms of various shapes and frequencies depending upon the application. Similarly, the transducers can be of various shapes and focal lengths. Moreover, in some instances, it may be preferred to employ a separate transmitter and receiver rather than a dual purpose transducer.

The invention can be used in imaging applications as well, such as in conjunction with conventional B-scan imaging to improve image contrast or as an additional parameter in the generation of 3 dimensional computer tomographs. Moreover, the various computations described herein can be performed using either digital or analog means, and the operations can be carried out by hardware, firmware, software and any combination of such means.

DETAILED DESCRIPTION

Figure 1:
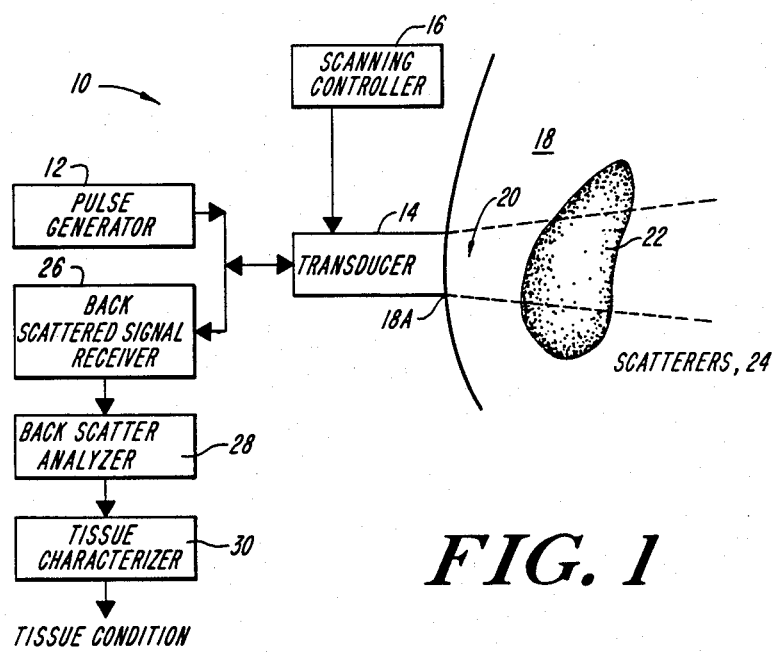
FIG. 1 is an overall schematic diagram of an ultrasonic characterization system according to the invention.

FIG. 1 shows an ultrasonic characterization system 10, including a pulse generator 12 and a transducer 14 under control of a scanning controller 16 adapted for positioning on an accessible surface 18A of a patient or other material to transmit an acoustic signal 20 (e.g., of about 1 microsecond with a periodicity of about 1 millisecond) into the body 18. (Acoustic scanning can be accomplished by mechanical translation of a single transducer element or by sequential activation of transducer elements in an array, or properly phasing an array for scanning.) In the body 18, the pulse signal 20 encounters scatterers 24 within a tissue-of-interest 22 which can be, for example, an organ, such as the liver, pancreas, kidney, or other body structure, such as bone or muscle tissue. A scattered signal is sensed by transducer 14 and routed to a backscattered signal receiver 26 (e.g., a A/D converting sampler), analyzer 28 and tissue characterizer 30 to estimate and characterize the type and/or condition of the tissue 22.

Figure 2:
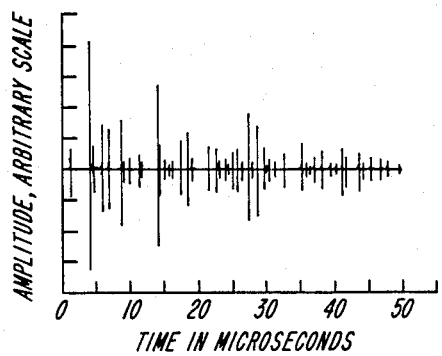
FIG. 2 is a typical backscatter signal obtained with the system of FIG. 1 when the transducer transmits a short duration pulse.

When an incident acoustic pulse interacts with the tissue 22, reflections occurring at each of the randomly spaced and randomly reflecting scatterers 24 result in a complicated signal received by the transducer, as exemplified in FIG. 2. Suppose the transducer is located at spatial coordinates (x,y,z=0) and the receiver signal as a function of time, t, is denoted r(x,y,t). This backscattered signal can be written as $$r(x,y,t) = \sum_{i=1}^{\infty} a_i u(x; X_i, y; Y_i, t; \tau_i \epsilon_i) \quad (1)$$

where $a_i$ and $\tau_i$ are the amplitude and propagation time associated with the $i^{th}$ scatterer. The terms $X_i$, $Y_i$ represent the spatial coordinates in the y-y plane of the $i^{th}$ scatterer, and $\epsilon_i$ is a set of random parameters for describing the functional form for u(•). The term u(•) represents the time-varying signal associated with the $i^{th}$ scattering component. The round-trip propagation times $\{\tau\}$ are assumed to occur in accordance with a non-homogeneous Poisson process with intensity $v(t)$.

Eq. 1 is sufficiently general to permit the incorporation of many physical effects. The amplitude coefficients, $a_i$, model the effects of random reflection coefficients within the medium. The time-varying nature of the individual wavelets, u(•), models effects such as attenuation, diffraction, complex beam patterns, and spatially-varying media statistics. Using the random parameters, $\epsilon$, allows near-field effects to be properly addressed. The use of a non-homogeneous Poisson process enables the modeling of spatially varying scatter number densities, and beam spreading. Although it is possible to model the Dopler effects due to motion of the individual scatterers, it will be assumed, for the sake of simplicity, that there is no appreciable scatterer motion. For tissue applications, this assumption will exclude modeling of backscatter from in-vivo cardiac tissues.

A somewhat simplified formulation can be used to describe the wavelets, $u_i$(•). It can also assume that each wavelet is stationary and has the same spatial/temporal response of the form, $$u(\bullet) = f(x_i, y_i) \bullet h(t - \tau_i) \quad (2)$$

where $f(x_i,y_i)$ is the beam-pattern function (bpf) of the system, h(t) is the system temporal response, and $(x_i, y_i)$ are the spatial coordinates of the $i^{th}$ scatterer. The product of the bpf and h(t) is commonly referred to as the system point-spread function (psf). By making the assumptions leading to Eq. 2, the signal r(t) is approximately stationary over relatively short time intervals. Non-stationary effects, e.g., attenuation, can then be accounted for by applying different versions of Eq. 2 to different time-segments of r(t). One can additionally assume that over this short time interval the SND is constant. This has the physical interpretation that the scatterers are randomly distributed in a uniform manner throughout the segment volume. These approximations marginally reduce the generality of Eq. 1 and greatly reduce the complexity of the notation.

Suppose N samples of the process r(t) are acquired and denoted $r_i$. The sample second and fourth order moments, $S_2$ and $S_4$, are given by $$S_2 = (1/N) \sum_{i=1}^{N} r_i^2 \quad (3)$$

$$S_4 = (1/N) \sum_{i=1}^{N} r_i^4 \quad (4)$$

The SND estimate, $\widehat{SND}$, can then be expressed as $$\widehat{SND} = \frac{F_m F_s}{(K - 3)} \quad (5)$$

where $F_m$ and $F_s$ are medium and system dependent constants, respectively, and K is the kurtosis. The quantity (K−3) is often referred to as the "coefficient of excess," $\gamma$. These parameters are defined as follows:

$$K = S_4/S_2^2 \quad (6)$$

$$F_m = E[a^4]/E^2[a^2] \quad (7)$$

$$F_s = \frac{2 \int\int\int_{-\infty}^{\infty} f^4(x,y) \cdot h^4(t)\, dx\, dy\, dt}{c\left\{\int\int\int_{-\infty}^{\infty} f^2(x,y) \cdot h^2(t)\, dx\, dy\, dt\right\}^2} \quad (8)$$

where c is the acoustic sound speed of the tissue and E[•] denotes probabilistic expectation.

The kurtosis alone is typically insufficient for determination of the SND. This is because the medium dependent factor $F_m$ (which depends on the statistics of the random reflectors) and the system dependent factor $F_s$ (which is inversely proportional to the volume of the psf) must be known. Equivalently, the kurtosis, although suggested as a tissue characterization parameter, is inappropriate for such use because it is system dependent. To understand the nature of $F_m$ and $F_s$, theoretical expressions have been derived for cases representative of conditions found in medical ultrasonic work. For non-random $a_i$ and zero-mean Gaussian-distributed $a_i$, the values for $F_m$ are 1 and 3, respectively. Ultrasonic systems typically have a Gaussian-shaped psf, i.e., $$f(x,y) \cdot h(t) = \exp(-(x^2+y^2)/L^2)\exp(-t^2/T^2)\cos(\omega_0 t) \quad (9)$$

where L is a measure of the spread of the beam profile, T is a measure of the temporal duration of the pulse, and $\omega_0$ ($\omega_0 \gg 1/T$) is the radian center frequency. Substituting Eq. 9 into Eq. 8 yields, $$F_s = \frac{3}{\pi\sqrt{\pi L^2 cT}} \quad (10)$$

Figure 3:
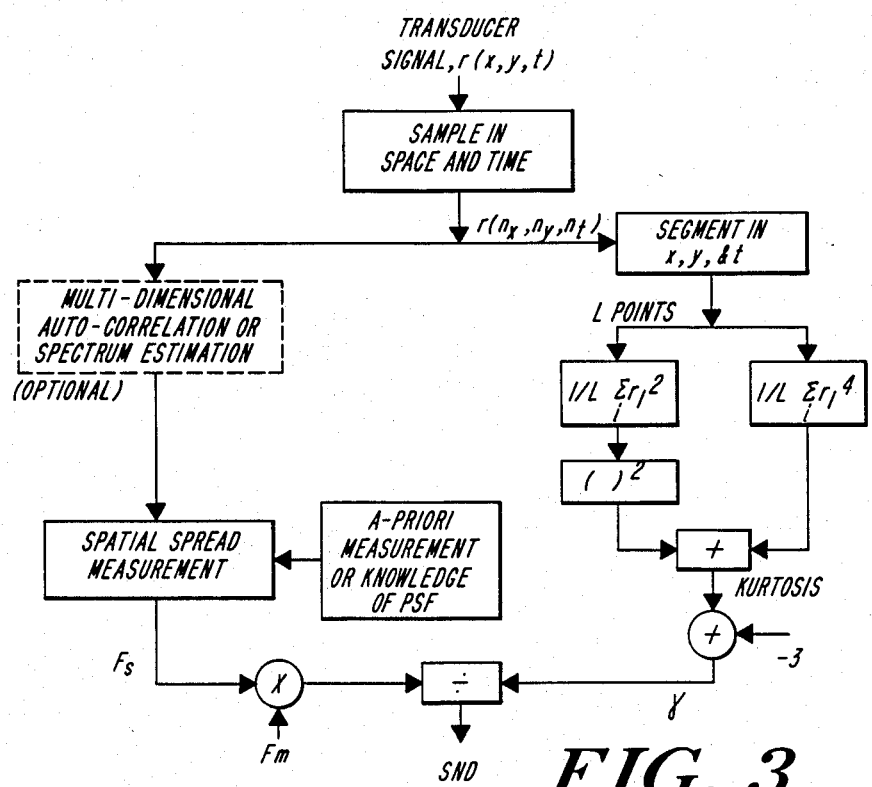
FIG. 3 is a block diagram representation of a method for estimating the scatterer number density (SND) according to the invention.

A general digital signal processing technique for performing SND estimation is depicted in FIG. 3. The first step of the method involves sampling of the process in both space and time and proper segmentation for computation of the moments. Sampling in time is generally performed with a high speed A/D converter and performed directly on the r.f. waveforms. Spatial sampling can be performed by either mechanical lateral scanning of the transducer or by scanning with a phased array. In general, samples in time and space will be combined to form the sample moments. The size of the segmented region for computation of a single SND estimate is chosen to be sufficiently small such that non-stationary effects are negligible in that region.

The second aspect of the SND method involves estimation of the parameters $F_s$ and $F_m$. The medium factor, $F_m$, if not known, can be assumed. This is not a problem for tissue characterization purposes since the SND estimate, although biased, is biased by a medium-dependent factor. The system dependent factor, $F_s$, must be known, however, in order to achieve consistent experimental results. $F_s$ can be determined directly from a knowledge of the resolution cell (volume of the system point spread function). Several methods are proposed for obtaining $F_s$. The first involves a-priori measurement of the psf. With this method, a point scatterer is scanned in a water-tank setup, and the response as a function of space and time is measured. The second approach is to infer $F_s$ from theoretical relationships for the transducer point spread function. This method is particularly attractive for phased-array scanners since the psf can be controlled by proper apodization of the array. The third method proposed for estimating $F_s$ is to infer it directly from the backscattered signals and is indicated by FIG. 3 by the dashed box. This approach is attractive since it is data adaptive and is not affected by phenomena which would cause the in-situ psf to differ from the water-tank measured psf. This method is based on the fact that the correlation function of the backscattered process is directly related to the in-situ psf.

The auto-correlation function of the backscattered signals is in fact proportional to the auto-correlation of the psf. In general, the spread of the psf correlation function will be more than the spread of the psf, itself. Additionally, the mathematical form of the auto-correlation function will differ from the mathematical form for the psf. The psf of practical importance is the Gaussian-shaped psf. It can be easily shown that the auto-correlation function of the psf for this case is also Gaussian, but with twice the spatial spread. Hence, determination of F, is a simple matter provided the spread of the auto-correlation function has been measured properly.

Figure 4:
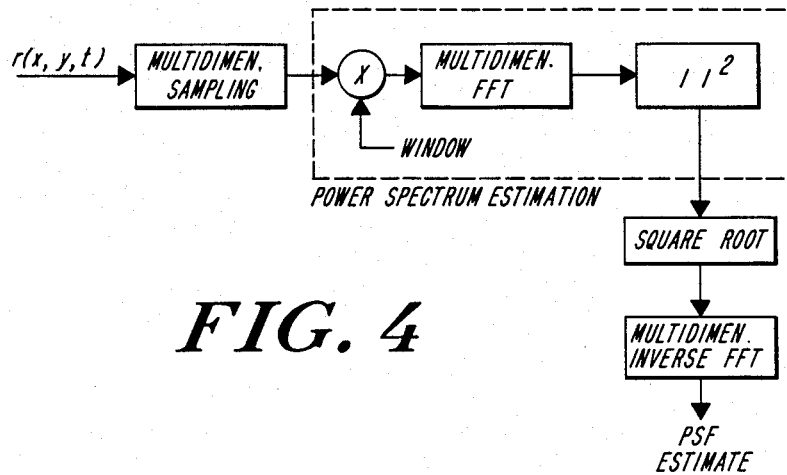
FIG. 4 is a block diagram representative of a method for estimating the point spread function according to the invention.

The previous paragraphs have been concerned with estimating the auto-correlation function of the psf from which the spread of the psf could be inferred. An alternative approach is to estimate the psf directly. The psf can be directly estimated by taking the inverse-Fourier transform of the square root of the multi-dimensional power-spectrum estimate, as depicted in FIG. 4. Provided that the psf is a zero-phase function, then this operation will result in a true estimate of the psf. When the psf is not zero phase, this method is still useful since only the spread of the psf is of interest (i.e., psf phase is unimportant for SND estimation). An additional feature of this approach is that for the case in which the psf is random, the estimated psf is in fact the average psf in the volume considered. Thus, since only the spatial averaged psf is needed, the data-adaptive approach is quite appropriate.

An extensive experimental investigation was undertaken to verify the methods disclosed herein. The experimental apparatus was a mini-computer based data acquisition and control system consisting of a DEC PDP 11/23 computer, a Biomation 8100 transient recorder, and a computer-controlled translator. Additionally, the technique for SND estimation was implemented on the digital computer system to operate on either stored digitized waveforms or on acquired waveforms in real-time. (It should be clear, however, that dedicated analog hardware can also perform the functions described above.)

Acoustic scattering phantoms were developed and constructed. The phantoms used a gelatin-based matrix in which randomly sized microspheres were suspended. The gelling process was performed in an open-ended plexiglass cylinder 14 cm in diameter and 6 cm in depth with the ends covered by a transparent plastic film. The microspheres used were manufactured by Poly-sciences Corp. and are termed "Poly-Glas beads." These spherical, polystyrene beads are coated with glass and have a net density of 1.03 g/cc. The size of the beads ranged from about 90 to about 150 microns with an average diameter of 120 microns.

In order to obtain known acoustic scatter properties in the phantom, the number of scatterers added to the gelatin base must be known. An approximation for the weight of microspheres required in a phantom of volume V to produce a desired SND is $$\text{Weight of beads in mg} = \frac{SND \cdot V \rho \pi \phi^3}{6 \times 10^9} \quad (11)$$

where $\rho$ is the density (g/cc) of the microspheres and $\phi$ is the average sphere diameter (microns). The different gelatin-based phantoms were constructed with computed SND values of 10, 20, 30, 40, 60, 80, 100, 200, 400, and 800 scatterers/cm3.

Three different tissue specimens were used in this investigation; bovine muscle, bovine liver, and pig liver. Each specimen was excised 24–28 hours prior to the experiments and was refrigerated at a temperature of 5° C. For the experiments, each specimen was cut into a cube 6 cm per side and placed in partially-degassed saline solution at 22° C.

Figure 5A:
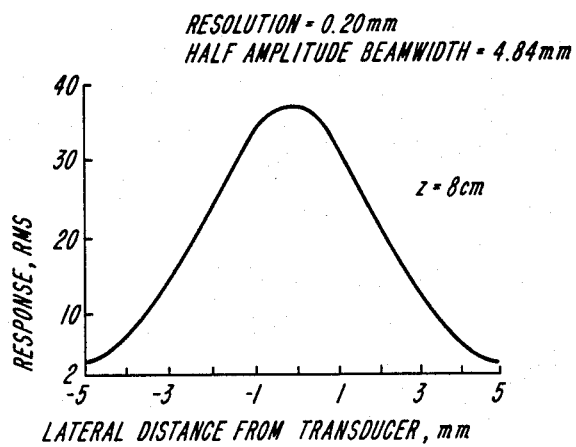
FIGS. 5A and 5B are graphs showing a typical acoustic beam profile and frequency response, respectively, of an illustrative transducer operated in accordance with the invention.
Figure 5B:
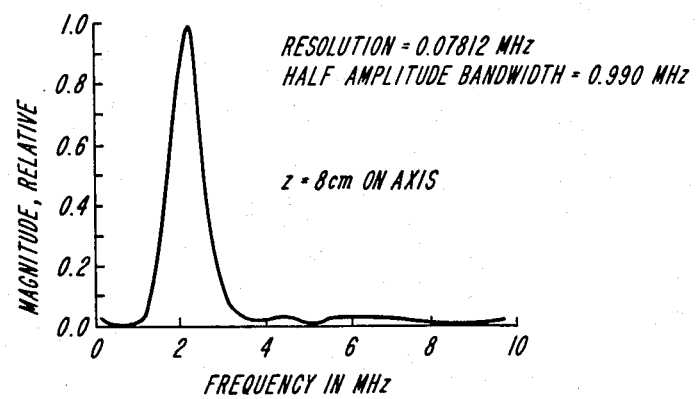

Several different ultrasonic transducers were used in the experimental studies so that the SND algorithm could be verified to be system independent. The transducers were chosen to give a variety of acoustic field characteristics. It was found that the transducers often exhibited a Gaussian shaped psf. A cross-section of a typical measured psf and the associated frequency response is shown in FIGS. 5A and 5B, respectively.

The psf was measured for each transducer by a water-bath scanning approach. The psf was formed by scanning the transducer over an appropriate reference scatterer and measuring the r.m.s. response and frequency spectrum at each position. The reference scatterer was the tip of a 150 $\mu$m diameter wire. From these measurements, a sampled three-dimensional beam profile and frequency response was formed. For each 0.5 cm in range, measurement of the average beamwidth was used to calculate L, and measurement of the average bandwidth enabled calculation of T. Values of $F_s$ for each 0.5 cm in range could then be calculated using the relationship in Eq. 10. A summary of the psf measurements is given in Table 1.

The experimental arrangement for the acquisition of the backscattered signals consisted of placing both the transducer and phantom/specimen in a water/saline bath and positioning both such that multiple echoes within the tank would not appear in the backscattered waveforms. Backscattered waveforms were obtained by averaging 50 or 75 signals at each transducer location in order to reduce quantization and background noise. For each phantom 225 backscattered ensemble waveforms were acquired by literal translation of the transducer. Lateral scanning was performed in plane with 15 points to a side such that the spacing between scans was 5.0 mm for the phantoms and 2.5 mm for the tissues. The signals were sampled at a 20 MHz rate and 1024 points were stored from each of the 235 waveforms.

Figure 6A:
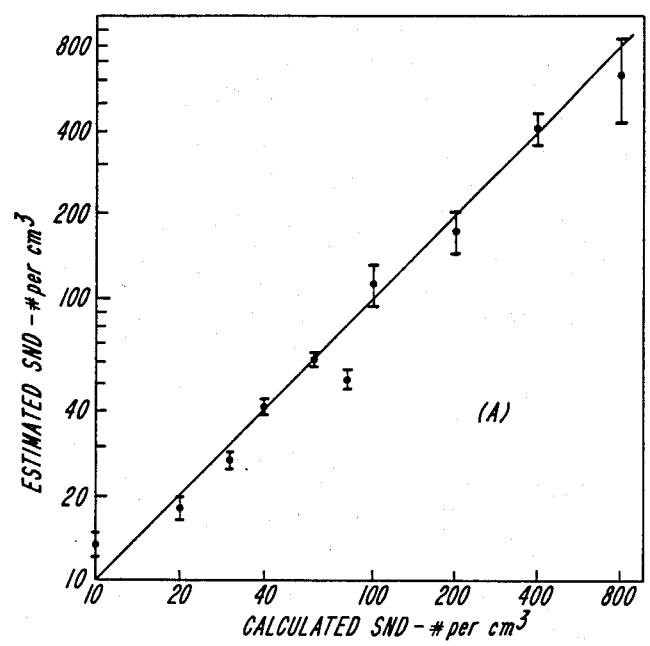
FIGS. 6A and 6B are a graphic illustration of SND estimation results for microsphere/gelatin phantoms using different transducers in the practice of the invention. Error bars indicate the standard deviation of the mean.
Figure 6B:
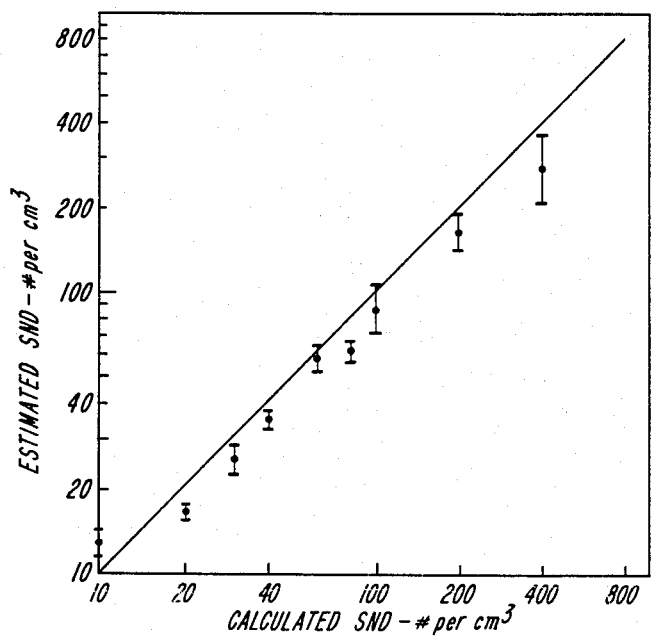

The backscattered signals obtained from the phantoms and the tissues were processed using the proposed SND algorithm. The segmentation involved 40 points from each waveform yielding a total of 40×225=9000 samples per moment calculation. Twenty $\gamma$ estimates were calculated from 3 cm of data in the range direction beginning with 1 cm below the phantom (specimen) surface. These were converted to SND estimates by using the measured $F_s$ value for the range considered. Additionally, the values of $F_m$ used in the calculations were assumed to be 1 and 3 for the phantoms and tissues, respectively. The estimated SND results for the tissue specimens are given in Table 2, and the results for the gelatin phantoms are shown in FIGS. 6A and 6B using transducer 3 and transducer 4 from Table 1, respectively.

TABLE 2

| Results for in-vitro Tissue Experiments | | | |
|---|---|---|---|
| Specimen | Transducer | SND (#/cc) | relative uncertainty of mean (%) |
| Pig | 1 | 94 | 8 |
| Liver | 2 | 109 | 10 |
| Bovine | 1 | 491 | 14 |
| Liver | 2 | 613 | 13 |
| Bovine Muscle across fibers | 1 | 110 | 12 |
| | 2 | 98 | 9 |
| Bovine Muscle along fibers | 1 | 211 | 11 |
| | 2 | 185 | 11 |

The experimental results obtained from the phantoms confirm that the SND estimation methods disclosed herein can, in fact, estimate the SND of a randomly scattering medium. Most importantly, the SND estimates appear to be independent of the ultrasonic field characteristics. In most cases, the measured value of SND is well within two standard deviations of the mean of the calculated SND.

The uncertainty in the SND estimates for the phantoms increased as the SND increased. For higher SND, the number of scatterers within the range cell becomes large, and the backscattered waveforms tend towards a Gaussian process. Since the SND estimate obtained from Eq. 5 essentially relies on measuring the deviation from a Gaussian process, it would be expected that larger SND values would result in larger estimate uncertainty. Additionally, it is seen that the transducer with the smaller resolution cell (#3) exhibits better performance of this same reason.

The SND estimates obtained for the tissue samples generally exhibit a statistically significant difference among tissue types. Additionally, the SND estimates obtained from two different transducers yielded no significant differences in the SND estimates. Histological analysis of the tissue samples indicated that the estimated SND values are correlated with the average

TABLE 1

| Measured acoustic field properties for ultrasonic transducers used in the experiments | | | | | |
|---|---|---|---|---|---|
| Transducer Description | Range Considered from Xducer (cm) | Center Freq. nominal (MHz) | 6 dB Bandwdth, range (MHz) | 6 dB Beamwdth, range (MHz) | Fs average |
| 1. 0.5" diam., focus at 8 cm, Panametrics V309 | 8.0 to 12.0 (focus/far field) | 5.0 | 2.2 to 2.4 | 2.1 to 3.4 | 599 |
| 2. 0.75" diam., focus at 8 cm, Panametrics V305 | 8.0 to 12.0 (near/focused) | 2.5 | 1.8 to 1.9 | 2.3 to 3.4 | 426 |
| 3. 0.5" diam., Aerotech Gamma | 8.0 to 12.0 (far field) | 2.3 | 0.9 to 1.0 | 4.8 to 6.8 | 53.7 |
| 4. 0.75" diam., Custom-made | 8.0 to 12.0 (near/far field) | 1.3 | 0.5 to 0.7 | 5.6 to 8.0 | 26.0 | cell-spacing of the specimens. This correlation was particularly dominant for the pig liver which had a hexagonal-shaped lobular structure with mean spacing of approximately 2 mm. This is consistent with the SND estimate since the cube root of the estimate predicts an average cell size of 2.15 mm.

The present invention can be applied to describe a wide variety of acoustic-medium interactions. This diversity arises from the fact that the scattering process and, if desired, the response of the acoustic system, can be treated as non-stationary, stochastic processes. Hence, the method can be useful in deriving tissue estimators and their performances, as well as describing the process of acoustic image formations. The method has been shown to reduce to models which assume Gaussian backscatter statistics (large SND case). In addition, the method appropriately accounts for non-Gaussian statistics which have been observed in backscatter from tissue structures. An added feature of the method is that its statistical nature is appropriate for describing in-vivo backscatter processes.

The SND estimation scheme disclosed herein can arrive at estimates of a tissue-dependent property which are independent of the measurement system, easily computed, unbiased and consistent. For both the phantom and tissue estimates, it is seen that the fractional uncertainty is of the order of 10%. These results were obtained, however, by using very coarse sampling in the spatial dimension. Clearly, the use of higher frequency focused transducers, accompanied by fine sampling, can result in a comparable error using considerably less scanning volume. It appears that a fractional uncertainty of 10% can be obtained using current ultrasonic transducer technology over a scan volume as small as 1 $cm^3$. Additionally, it appears that SND values may vary considerably among tissue types. Data by others indicate differences as large as 20% in scatterer separation among different human tissue types. This suggests that there may be as large as a 60% difference in SND values among different human tissue types. If this is true, then SND would be a particularly attractive tissue characterization parameter since it would allow reasonably accurate estimates with a minimal volume of interrogated tissue.

Further description of various embodiments of the invention and experimental results, as well as technological background materials, can be found in Appendix A, the doctoral thesis of Gerald E. Sleefe, one of the co-inventors herein, submitted herewith and incorporated by reference.

What is claimed is:

1. A method for non-invasive characterization of tissue, the method comprising:
    transmitting an acoustic signal to a tissue;
    receiving a backscattered waveform from said tissue;
    analyzing said backscattered waveform as a sum of individual scatterer components to assign a scatterer number density to said tissue; and
    characterizing said tissue by comparing said assigned scatterer number density with predetermined parameters to obtain an identification of the tissue character.

2. The method of claim 1 wherein the step of transmitting an acoustic signal further includes scanning a region of said tissue.

3. The method of claim 1 wherein the step of analyzing a backscattered waveform further includes averaging a plurality of backscattered waveforms.

4. The method of claim 1 wherein the step of analyzing a backscattered waveform further includes measuring a spatial spread of said waveform by auto correlation.

5. The method of claim 1 wherein the step of analyzing the backscattered waveform further includes measuring a kurtosis obtained from statistical moments of said backscattered waveform and comparing a coefficient of excess with a measurement of a volume associated with a system point spread function.

6. An apparatus for non-invasive characterization of tissue, the apparatus comprising:
    means for transmitting an acoustic signal to a tissue;
    means for receiving a backscattered waveform from said tissue;
    means for analyzing said backscattered waveform as a sum of individual scatterer components; and
    means for characterizing said tissue by comparing a scatterer density number with predetermined parameters to obtain an identification of the tissue character.

7. The apparatus of claim 6 wherein the transmitting means further includes a pulse generating means electrically connected to a transducer for generating an acoustic pulse at a surface of said transducer.

8. The apparatus of claim 6 wherein the transmitting means further include an array of transducers and means for selectively activating said transducers to scan a volume of said tissue.

9. The apparatus of claim 6 wherein the transmitting means further includes a transducer end translating means for translating said transducer to scan a volume of said tissue.

10. The apparatus of claim 6 wherein the receiving means further includes a transducer for converting said backscattered waveform into an electrical signal.

11. The apparatus of claim 10 wherein the receiver means further includes means for sampling said electrical signal.

12. The apparatus of claim 11 wherein the sampling means further includes an analog-to-digital converter.

13. The apparatus of claim 11 wherein the sampling means further includes averaging means for averaging a plurality of backscattered waveforms.

14. The apparatus of claim 6 wherein the analyzing means further includes computer means for calculating a kurtosis from statistical moments of the backscattered waveform and for comparing a coefficient of excess with a measurement of a volume associated with a system point spread function.

15. The apparatus of claim 14 wherein the computer means further includes an auto correlation means for measuring a spatial spread of said waveform.

16. The apparatus of claim 14 wherein the apparatus further includes calibration means for a-priori measurement of the system point spread function.

17. The apparatus of claim 6 wherein the characterizing means further included comparison means for comparing said scatterer density number with stored values derived from known histological tissue conditions.

18. The apparatus of claim 6 wherein the analyzing means further includes a programmed microprocessor.

19. The apparatus of claim 6 wherein analyzing means further includes analog hardware.

20. A method for non-invasive characterization of tissue, the method comprising:
    transmitting an acoustic signal to a tissue;
    receiving a backscattered waveform from said tissue;

analyzing said backscattered waveform as a sum of individual scatterer components to assign a scatterer number density to said tissue, said scatterer number density being inversely proportional to a coefficient of excess of said backscattered waveform; and characterizing said tissue by comparing said assigned scatterer number density with predetermined parameters to obtain an identification of the tissue character.

21. The method of claim 20, wherein said analyzing step includes the step of determining said coefficient of excess of said waveform.

22. The method of claim 21, wherein said analyzing step further includes the step of determining a volume of a system point spread function.

23. The method of claim 22, wherein said analyzing step further includes the step of combining said coefficient of excess and said volume of the point spread function to determine an estimate of said scatterer number density.

24. The method of claim 23, wherein said combining step includes the step of generating an estimate of said scatterer number density which is proportional to said volume of said point spread function and inversely proportional to said coefficient of excess.

25. An apparatus for non-invasive characterization of tissue, the apparatus comprising:

means for transmitting an acoustic signal to a tissue;

means for receiving a backscattered waveform from said tissue;

means for analyzing said backscattered waveform as a sum of individual scatterer components and for generating a scatterer number density of said tissue, said scatterer number density being inversely proportional to a coefficient of excess of said backscattered waveform; and means for characterizing said tissue by comparing said scatterer number density with predetermined parameters to obtain an identification of the tissue character.

26. The apparatus of claim 25, wherein said analyzing means includes means for determining said coefficient of excess of said waveform.

27. The apparatus of claim 26, wherein said analyzing means further includes means for determining a volume of a system point spread function.

28. The apparatus of claim 27, wherein said analyzing means further includes means for combining said coefficient of excess and said volume of the point spread function to determine an estimate of said scatterer number density.

29. The apparatus of claim 28, wherein said combining means further includes means for generating an estimate of said scatterer number density which is proportional to said volume of said point spread function and inversely proportional to said coefficient of excess.

* * * * *